United States Patent [19]
Sakamoto et al.

[11] Patent Number: 6,121,264
[45] Date of Patent: Sep. 19, 2000

[54] IMIDAZOLE-SUBSTITUTED QUINOXALINEDIONE DERIVATIVES

[75] Inventors: Shuichi Sakamoto; Junya Ohmori; Jun-ichi Shishikura; Masamichi Okada; Masao Sasamata, all of Ibaraki, Japan

[73] Assignee: Yamanouchi Pharmaceutical Co., Ltd., Tokyo, Japan

[21] Appl. No.: 09/194,750

[22] PCT Filed: Jun. 5, 1997

[86] PCT No.: PCT/JP97/01905

§ 371 Date: Dec. 2, 1998

§ 102(e) Date: Dec. 2, 1998

[87] PCT Pub. No.: WO97/46555

PCT Pub. Date: Dec. 11, 1997

[30]    Foreign Application Priority Data

Jun. 6, 1996   [JP]   Japan ................................... 8-144282

[51] Int. Cl.[7] ..................... A61K 31/498; C07D 403/10; C07D 403/14
[52] U.S. Cl. ........................... 514/249; 544/354
[58] Field of Search ............................... 544/354; 514/249

[56]    References Cited

U.S. PATENT DOCUMENTS

| | | | |
|---|---|---|---|
| 5,714,489 | 2/1998 | Lubisch et al. | 514/249 |
| 5,750,525 | 5/1998 | Huth et al. | 514/249 |
| 5,849,743 | 12/1998 | Lubisch et al. | 514/249 |

FOREIGN PATENT DOCUMENTS

| | | |
|---|---|---|
| 0 784 054 A1 | 7/1997 | European Pat. Off. . |
| 7165756 | 6/1995 | Japan . |
| 8003160 | 1/1996 | Japan . |
| 8291071 | 11/1996 | Japan . |
| 94/25469 | 11/1994 | WIPO . |
| 9426737 | 11/1994 | WIPO . |
| 96/10023 | 4/1996 | WIPO . |

OTHER PUBLICATIONS

L. Turski et al., "Pharmacology of ZK200775 and ZK202000, Competitive Non–NMDA Glutamate Receptor Antagonists", *Soc. Neurosci. Abstr.*, Abstract No.604.6, vol. 22, Part 2, P. 1529, 1996.

*Primary Examiner*—Emily Bernhardt
*Attorney, Agent, or Firm*—Sughrue, Mion, Zinn, Macpeak & Seas, PLLC

[57]    ABSTRACT

Imidazole-substituted quinoxalinedione derivatives represented by the following general formula (I) or pharmaceutically acceptable salts thereof and pharmaceutical compositions useful as glutamate receptor antagonists and the like, which comprise said compounds or salts thereof and pharmaceutically acceptable carriers.

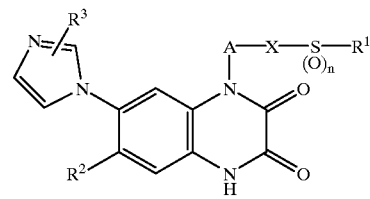

(Each symbol in the formula has the following meaning:

A: a group represented by a formula $(CH_2)_m$ or a group represented by a formula $Ph-(CH_2)_p$ (Ph: a phenyl group), X: an oxygen atom or a group represented by a formula $NR^4$, $R^1$: a hydrogen atom, a hydroxyl group or a triazolyl group, with the proviso that X may be a bond when $R^1$ is a triazolyl group, $R^2$: a hydrogen atom, a nitro group, a halogeno-lower alkyl group, a cyano group, an amino group, a mono- or di-lower alkylamino group or a halogen atom, $R^3$ and $R^4$: may be the same or different from each other and each represents a hydrogen atom or a lower alkyl group, n: 0, 1 or 2, m: an integer of 2 to 6, and p: an integer of 1 to 6.

9 Claims, No Drawings

IMIDAZOLE-SUBSTITUTED QUINOXALINEDIONE DERIVATIVES

TECHNICAL FIELD

This invention relates to an imidazole-substituted quinoxalinedione derivative or a salt thereof which has of glutamate receptor antagonism, particularly AMPA receptor and/or NMDA-glycine receptor antagonism, kainic acid neurotoxicity inhibition action and audiogenic seizure inhibition action, as well as excellent water-solubility and blood-solubility. It also relates to pharmaceutical compositions which comprise said imidazole-substituted quinoxalinedione derivative or a salt thereof and a pharmaceutically acceptable carrier, particularly a pharmaceutical composition which is useful as a glutamate receptor antagonist, an AMPA receptor antagonist, an NMDA-glycine receptor antagonist, a kainic acid neurotoxicity inhibitor, an anti-ischemia drug or a psychotropic drug.

BACKGROUND ART

Amino acids such as L-glutamic acid, L-aspartic acid are known to be central nerve system neurotransmitters. It is said that extracellular accumulation of these excitatory amino acids and their continuous excessive stimulation of to nerves lead to Huntington chorea, Parkinson disease, epilepsy, Alzheimer disease, senile dementia and neurodegeneration or deficiency in mental and motor functions observed after the condition of cerebral ischemia, oxygen deficiency or hypoglycemia.

In consequence, it has been considered that regulator of the abnormal activity of an excitatory amino acid is useful for the treatment of neurodegeneration and mental diseases, and it is considered also that such a drug will be effective for drug dependence and alcohol dependence.

Excitatory amino acids exhibit their action through glutamate receptors which are specific receptors existing at postsynaptic or presynaptic region. Such receptors are presently classified into the following three groups based on the electrophysiological and neurochemical studies.

1) NMDA (N-methyl-D-aspartate) receptors
2) non-NMDA receptors
    a) AMPA [2-amino-3-(3-hydroxy-5-methyl-4-isoxazolyl)propionic acid] receptor
    b) kainate receptor
3) metabotropic glutamate receptors The compound of the present invention has glutamate receptor antagonism (particularly, AMPA receptor antagonism), kainic acid neurotoxicity inhibition action and audiogenic seizure inhibition action, so that it is useful as an anti-ischemia drug or a psychotropic drug.

L-Glutamic acid and L-aspartic acid activate the aforementioned glutamate receptors and transmit excitation. Nervous disorders occur when an excess amount of NMDA, AMPA or kainic acid is allowed to act on nerves. It has been reported that 2-amino-5-phosphonovalerianic acid or 2-amino-7-phosphonoheptanoic acid as a selective antagonist against NMDA receptors is effective in nervous disorders induced by the action of NMDA and in experimental animal models suffering from epilepsy and cerebral ischemia (*J. Pharmacology and Experimental Therapeutics*, 250, 100 (1989); *J. Pharmacology and Experimental Therapeutics*, 240, 737 (1987); *Science*, 226, 850 (1984)).

It has been reported that NMDA receptors are allosterically regulated by glycine receptors (*EJP*, 126, 303 (1986)), and that a glycine receptor antagonist HA-966 is also useful in an experimental animal model suffering from cerebral ischemia (American Society for Neuroscience, 1989).

In addition, it has been reported that NBQX (6-nitro-7-sulfamoylbenzo[f]quinoxaline) which is a selective antagonist against the AMPA receptor is also useful in an experimental animal model suffering from cerebral ischemia (*Science*, 247, 571 (1990)).

On the other hand, it has been shown that all of the cloned non-NMDA receptors have affinity for kainic acid. Among these receptors, a receptor having low affinity for kainic acid (AMPA/kainate receptor) has been indicated to be related to the neuronal death at the time of ischemia such as cerebral infarction (P. C. May and P. M. Robison, *J. Neurochem.*, 60, 1171–1174 (1993)). This AMPA/kainate receptor has high affinity for AMPA too, but the binding sites of AMPA and kainic acid are not clear. However, it has been reported that AMPA and kainic acid show different electrophysiological responses to the AMPA/kainate receptor. It has been reported also that AMPA alone shows weak action in a neurotoxicity test which uses a neuronal culture system, but kainic acid induces by itself significant neuronal death in the test (P. C. May and P. M. Robison, *J. Neurochem.*, 60, 1171–1174 (1993)). In consequence, there is a possibility that a compound capable of showing kainic acid toxicity inhibition action in a neuronal culture system will strongly inhibit neuronal death induced by excess excitement caused by glutamic acid at the time of ischemia.

Several compounds have been reported as quinoxalinedione derivatives which show NMDA-glycine receptor antagonism and/or AMPA receptor antagonism, such as a compound having a —A—COR² group at the 1- or 4-position of the quinoxalinedione nucleus, represented by a formula

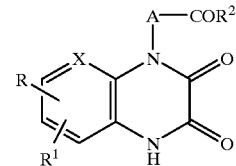

(wherein each symbol has the following meaning:

X: a nitrogen atom or a group represented by a formula CH,

R: an imidazolyl group or a di-lower alkylamino group,

R$^1$: (1) a halogen atom, a nitro group, a cyano group, a carboxy group, an amino group, a mono- or di-lower alkylamino group, a lower alkanoyl group, a lower alkylthio group, a lower alkylsulfinyl or a lower alkylsulfonyl group or a carbamoyl group, (2) a lower alkyl group or a lower alkoxy group, wherein these groups may be substituted with a halogen atom(s), a carboxy group(s) or an aryl group(s), or (3) a lower alkoxycarbonyl group or a phenyloxy group which may be substituted with a carboxy group, R$^2$: a hydroxyl group, a lower alkoxy group, an amino group or a mono- or di-lower alkylamino group, A: a lower alkylene group which may be substituted or a group represented by a formula —O—B—, and B: a lower alkylene group, with the proviso that a case in which R is an imidazolyl group, R$^1$ is a cyano group, A is an ethylene group and R$^2$ is a hydroxyl group is excluded) (International Patent Publication WO 96/10023 (to be referred to as reference 1 hereinafter)), a compound having a —(CH$_2$)$_n$—CR$^2$H—(CH$_2$)$_m$—Z group at the 1- or 4-position of the quinoxalinedione nucleus, represented by a formula

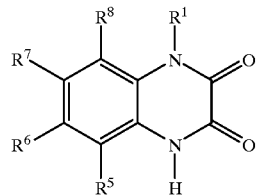

[wherein,

R$^1$ represents —(CH$_2$)$_n$—CR$^2$H—(CH$_2$)$_m$—Z,

R$^5$, R$^6$, R$^7$ and R$^8$ may be the same or different from one another and each represents a hydrogen atom, a C$_1$–C$_5$ alkyl group, CF$_3$, a nitro group, a halogen atom, NR$^9$R$^{10}$, a cyano group, SO$_p$R$^{11}$, SO$_2$NR$^{12}$R$^{13}$, SO$_3$H, a SO$_3$C$_1$–C$_6$ alkyl group or OR$^{14}$, wherein, R$^2$ represents a hydrogen atom or —(CH$_2$)$_q$—R$^3$, R$^3$ represents a hydrogen atom, a hydroxy group, a C$_1$–C$_6$ alkoxy group or NR$^{15}$R$^{16}$, n, m and q are respectively 0, 1, 2 or 3, Z represents POXY, OPOXY, OR$^{17}$, NR$^{18}$R$^{19}$, NH—COR$^{20}$, NH—SO$_2$R$^{21}$, SO$_2$R$^{22}$, SO$_2$R$^{23}$, a halogen atom, a cyano group or a tetrazole group, R$^{12}$, R$^{13}$, R$^{17}$ and R$^{23}$ respectively represent a hydrogen atom or a C$_1$–C$_4$ alkyl group and R$^{14}$ represents H or a C$_1$–C$_6$ alkyl group which is substituted 1 to 3 times with halogen atoms or unsubstituted, R$^{20}$ and R$^{21}$ respectively represent a C$_1$–C$_6$ alkyl group or a phenyl or a heteroaryl group which is substituted or not substituted with a halogen atom and R$^{22}$ represents a hydroxy group, a C$_1$–C$_4$ alkoxy group or NR$^{24}$R$^{25}$, R$^9$ and R$^{10}$ may be the same or different from each other and each represents a hydrogen atom, a CO-C$_1$–C$_6$ alkyl group, a phenyl group or a C$_1$–C$_6$ alkyl group, wherein these groups may be substituted with a C$_1$–C$_4$ alkoxy or an amino group optionally mono- or di-substituted with a C$_1$–C$_4$ alkyl or together with the nitrogen atom may form a 5- to 7-membered saturated heterocycle optionally having another N atom, S atom or O atom and may be substituted or an unsaturated 5-membered heterocycle which has 1 to 3 N atoms and may be substituted, and R$^{24}$ and R$^{25}$ may be the same or different from each other and each represents a hydrogen atom or a C$_1$–C$_4$ alkyl group, or together with the nitrogen atom may form a 5- to 7-membered saturated heterocycle optionally having another oxygen atom, sulfur atom or nitrogen atom and may be substituted, and represents an isomer or a salt thereof (see descriptions in the following patent publication for the meaning of other symbols)] (International Patent Publication WO 94/25469 (to be referred to as reference 2 hereinafter)), and other compounds described in International Patent Publication WO 92/07847 and International Patent Publication WO 93/08173.

DISCLOSURE OF THE INVENTION

The inventors of the present invention have conducted studies on quinoxalinedione derivatives further in detail and, as a result, found that a compound always having a

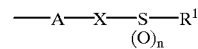

group at the 1- or 4-position of the nucleus of 7- or 6-imidazole-substituted quinoxalinedione is a novel compound which is not described in any of the prior art references and is also a highly useful compound as medicaments, because it shows more potent pharmacological actions (glutamate receptor antagonisms (AMPA receptor antagonism in particular), kainic acid neurotoxicity inhibition action, audiogenic seizure inhibition action and the like) in comparison with the prior art quinoxalinedione glutamate receptor antagonists and is also excellent in water-solubility and blood-solubility, and have accomplished the present invention on the basis of these findings.

Accordingly, the present invention relates to an imidazole-substituted quinoxalinedione derivative represented by the following general formula (I)

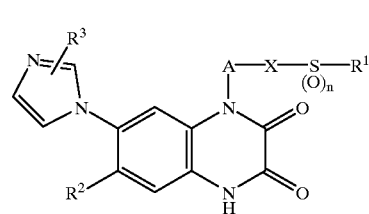

(wherein each symbol has the following meaning:

A: a group represented by a formula (CH$_2$)$_m$ or a group represented by a formula Ph—(CH$_2$)$_p$ (Ph: a phenyl group), X: an oxygen atom or a group represented by a formula NR$^4$, R$^1$: a hydrogen atom, a hydroxyl group or a triazolyl group, with the proviso that X may be a bond when R$^1$ is a triazolyl group, R$^2$: a hydrogen atom, a nitro group, a halogeno-lower alkyl group, a cyano group, an amino group, a mono- or di-lower alkylamino group or a halogen atom, R$^3$ and R$^4$: may be the same or different from each other and each represents a hydrogen atom or a lower alkyl group, n: 0, 1 or 2, m: an integer of 2 to 6, and p: an integer of 1 to 6) or a pharmaceutically acceptable salt thereof. The compound of the present invention has a characteristic from the viewpoint of its chemical structure that it always has a

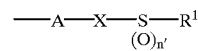

group at the 1- or 4-position of the nucleus of the 7- or 6-imidazole-substituted quinoxalinedione.

The present invention also relates to a pharmaceutical composition which comprises said imidazole-substituted quinoxalinedione derivative or a salt thereof and a pharmaceutically acceptable carrier. Particularly, it relates to a pharmaceutical composition which is useful as a glutamate receptor antagonist, an AMPA receptor antagonist, an NMDA-glycine receptor antagonist, a kainic acid neurotoxicity inhibitor, an anti-ischemia drug or a psychotropic drug.

The following describes the compound represented by the aforementioned general formula (I) further in detail.

According to the definition of the general formula of this specification, unless otherwise noted, the term "lower" means a straight or branched carbon chain having 1 to 6 carbon atoms.

Thus, illustrative examples of the "lower alkyl group" include alkyl groups having 1 to 6 carbon atoms such as a methyl group, an ethyl group, a propyl group, an isopropyl group, a butyl group, an isobutyl group, a sec-butyl group, a tert-butyl group, a pentyl (amyl) group, an isopentyl group, a neopentyl group, a tert-pentyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,1,2-trimethylpropyl group, a 1,2,2-trimethylpropyl group, a 1-ethyl-1-methylpropyl group, a 1-ethyl-2-methylpropyl group, of which alkyl groups having 1 to 3 carbon atoms are preferred.

The "mono- or di-lower alkylamino group" is an amino group substituted with 1 or 2 of the just described lower alkyl group(s), and its illustrative examples include mono-lower alkylamino groups such as a methylamino group, an ethylamino group, a propylamino group, an isopropylamino group, a butylamino group, an isobutylamino group, a sec-butylamino group, a tert-butylamino group, a pentyl (amyl)amino group, an isopentylamino group, a neopentylamino group, a tert-pentylamino group, and di-lower alkylamino groups such as a dimethylamino group, an ethylmethylamino group, a diethylamino group, a dipropylamino group, a diisopropylamino group, a dibutylamino group, a diisobutylamino group, of which an amino group, a methylamino group, an ethylamino group, a dimethylamino group and a diethylamino group are preferred.

The "halogen atom" means a fluorine atom, a chlorine atom a bromine atom or an iodine atom, the term "halogeno-lower alkyl group" means a group in which optional hydrogen atoms of the aforementioned "lower alkyl group" are substituted with 1 to 3 of the just described "halogen atom", and illustrative examples of the "halogeno-lower alkyl group", when the halogen atom is a fluorine atom, for example, include a fluoromethyl group, a trifluoromethyl group, a 2-fluoroethyl group, a 3-fluoropropyl group, a 2-fluoro-1-methylethyl group, a 4-fluorobutyl group, a 3-fluoro-2-methylpropyl group, a 5-fluoropentyl group, a 4-fluoro-3-methylbutyl group, a 6-fluorohexyl group and the like.

A preferred example of the compound (I) of the present invention is a compound in which A is a group represented by a formula $(CH_2)_m$, X is an oxygen atom, n is 2 and $R^1$ is a hydroxyl group.

Particularly preferred compounds are 4-[2,3-dioxo-7-(1H-imidazol-1-yl)-6-nitro-1,2,3,4-tetrahydroquinoxalin-1-yl]butanesulfate or a salt thereof; and 3-[2,3-dioxo-7-(1H-imidazol-1-yl)-6-nitro-1,2,3,4-tetrahydroquinoxalin-1-yl]propanesulfate or a salt thereof.

The compound (I) of the present invention exists in tautomer forms based on the quinoxalinedione nucleus. Depending on the groups, it may also exist in the form of optical isomers (optically active substances, diastereomers and the like). These isomers in separated or mixed forms are included in the present invention.

The compound (I) of the present invention forms salts with acids or bases. Examples of the salts with acids include acid addition salts with mineral or inorganic acids such as hydrochloric acid, hydrobromic acid, hydroiodic acid, sulfuric acid, nitric acid, phosphoric acid and the like or with organic acids such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid and the like.

Examples of the salts with bases include salts with inorganic bases such as sodium, potassium, magnesium, calcium, aluminum and the like or with organic bases such as methylamine, ethylamine, ethanolamine, lysine, arginine, ornithine and the like, as well as ammonium salts.

In addition, the compound (I) of the present invention may be obtained in the form of hydrates, solvates with ethanol and the like or as polymorphic substances having various crystalline forms depending on its physicochemical properties or production conditions. All of these hydrates, solvates with ethanol and the like and substances having various crystalline forms are included in the present invention.

(Production Method)

Compounds of the present invention and their salts can be produced by applying various synthesis methods making use of the characteristic features of their basic nuclei or kinds of substituents. The following describes their typical production methods.

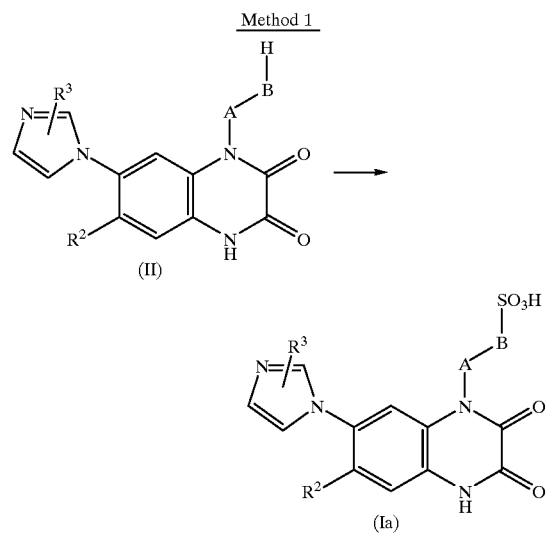

Method 1

(In the above reaction formula, A, $R^2$ and $R^3$ have the meanings described above, and B means an oxygen atom or a group represented by a formula NH.)

When an alcohol compound or amine represented by the general formula (II) is used as the starting compound, a compound of the present invention represented by the general formula (Ia) which is a sulfuric ester or a sulfamine derivative can be produced by allowing the starting compound to react with sulfuric acid, a halo-sulfuric acid or a complex of sulfur trioxide with a Lewis acid (for example, a pyridine-sulfate trioxide complex or the like), thereby effecting sulfuric esterification or sulfamination. In this connection, when $R^2$ is an amino group or a mono-lower alkylamino group, $R^2$ may also be sulfaminated in some cases, but sulfuric esterification or sulfamination of the side chain at the 1-position alone can be effected by optionally setting the reaction conditions such as reaction methods, amounts and the like.

It is desirable to carry out the reaction of compound (II) with sulfuric acid by dissolving the compound (II) in sulfuric acid under cooling and then gradually returning the temperature to room temperature. In this case, the reaction can be accelerated by adding fuming sulfuric acid or heating the reaction system. Also, the reaction can be effected by dissolving the compound (II) in an organic solvent such as dioxan, adding equivalent to excess amount of sulfuric acid (fuming sulfuric acid may be added as occasion demands) to the thus prepared solution which is cooled, gradually warming up the solution to room temperature and then, if necessary, heating the reaction system.

It is advantageous to carry out reaction of the compound (II) with a halo-sulfuric acid (for example, chlorosulfuric acid: $ClSO_3$ or the like) by dissolving the compound (II) in an organic solvent such as dimethyl sulfoxide (DMSO) which is inert to the reaction, adding 1 to 3 equivalents of the halo-sulfuric acid, preferably in the presence of an appropriate amount of Lewis acid such as triethylamine, and then effecting the reaction under a temperature condition of from cooling to heating.

It is desirable to carry out the reaction of compound (II) with a sulfur trioxide-Lewis acid complex by dissolving the compound (II) in an organic solvent which is inert to the reaction, preferably Lewis acid such as triethylamine which can dissolve the starting compound, adding the sulfur trioxide-Lewis acid complex as sulfur trioxide in chemical equivalent to excess amount and then effecting the reaction under a temperature condition of from cooling to heating, preferably at the heating reflux temperature.

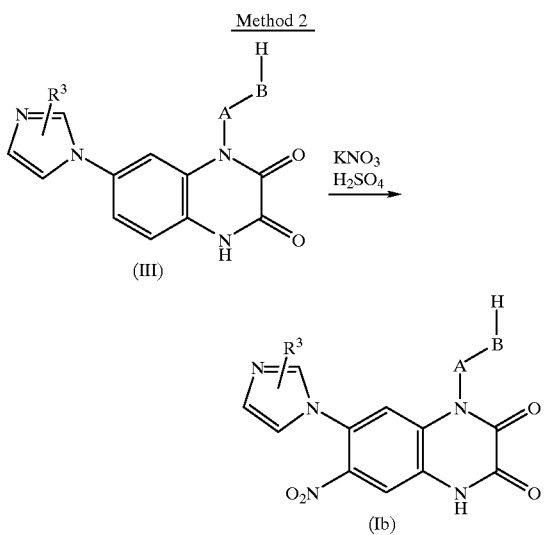

(In the above reaction formula, symbols A, B and $R^3$ have the meanings described above.)

A compound of the present invention represented by the general formula (Ib) which is a sulfuric ester or a sulfamine derivative that has a nitro group as $R^2$ can be produced by using a 7-position-unsubstituted compound (III) as the starting compound and simultaneously carrying out aromatic nitration and sulfuric esterification or sulfamination.

It is advantageous to carry out the reaction by dissolving the compound (II) in sulfuric acid under cooling, adding a nitration agent such as potassium nitrate to the solution and then gradually warming up the reaction mixture to room temperature.

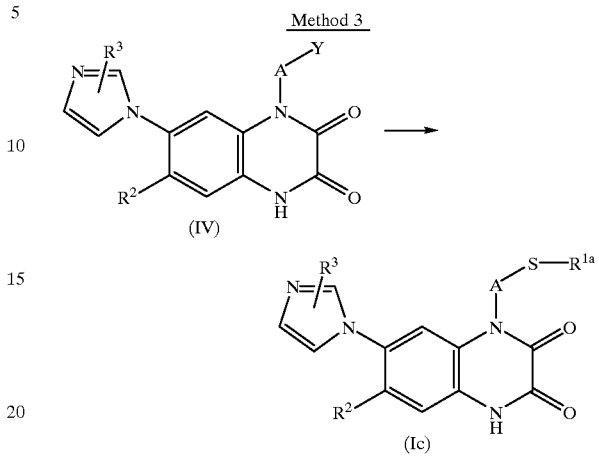

(In the above reaction formula, A, $R^2$ and $R^3$ have the meanings described above, Y means a halogen atom and $R^{1a}$ means a hydrogen atom or a triazolyl group.)

When a halo-compound (IV) is used as the starting compound, a compound of the present invention (Ic) in which $R^1$ is a hydrogen atom or a triazolyl group can be obtained by allowing the compound (IV) or a salt thereof to react with mercaptotriazole or an alkali metal salt thereof or with hydrogen sulfide or an alkali metal sulfide, thereby effecting thio-etherification or thiol formation. In this connection, it is desirable to produce a compound (Ic) of interest in which $R^2$ is an amino group or a mono- or di-lower alkylamino group, by carrying out the reaction using the compound (IV) in which $R^2$ is a nitro group and then carrying out a reduction reaction which will be described later or further carrying out N-alkylation, but thio-etherification or thiol formation of the side chain at the 1-position alone can be effected by optionally selecting a reaction condition such as introduction of a protecting group to prevent side reactions as much as possible.

In this case, iodine atom, bromine atom, chlorine atom and the like can be exemplified as the halogen atom, and bromine atom and chlorine atom are particularly preferred.

It is desirable to carry out the thio-etherification reaction using reaction-corresponding amounts of the reactants, or one of them in an excess amount, in a reaction-inert organic solvent such as dimethylformamide (DMF), DMSO or the like in the presence, when a thiol compound is used as the starting compound, of a base such as potassium carbonate, sodium hydride, potassium hydroxide or the like at room temperature or with heating, preferably with heating under reflux.

The thiol formation reaction can be carried out advantageously using reaction-corresponding amounts of the reactants, or one of them in an excess amount, in water or a reaction-inert organic solvent at room temperature or with heating.

Method 4

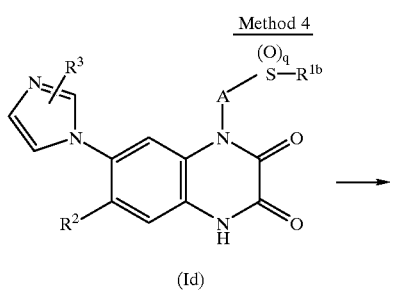

(Id)

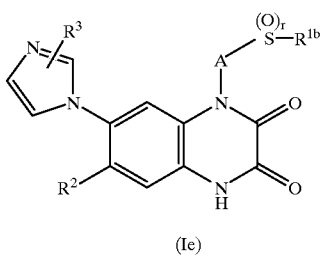

(Ie)

(In the above reaction formula, A, $R^2$ and $R^3$ have the meanings described above, $R^{1b}$ is a triazolyl group, q is 0 or 1 and r is 1 or 2.)

Among the compounds of the present invention, a triazolyl sulfoxide or triazolylsulfone compound (Ie), when a corresponding thioether (sulfide) or triazolyl sulfoxide compound (Id) is used as the starting compound, can be produced by the oxidation of the starting compound.

The oxidation reaction can be carried out in accordance with the usually used methods, and the sulfoxide compound can be obtained from the sulfide, or the sulfone compound from the sulfoxide compound, when one equivalent of an oxidizing agent is used, or the sulfone compound can be obtained from the sulfide when two equivalents of an oxidizing agent is used, in the presence, as occasion demands, of an acid catalyst such as dimethylformamide (DMF), DMSO or the like or a metal catalyst such as a salt of a vanadium tungsten, molybdenum, titanium, chromium or the like (e.g., vanadium pentoxide). With regard to the oxidizing agent to be used, hydrogen peroxide and various other peroxides generally used in the oxidation of sulfide and sulfoxide can be used in the same manner, and hydrogen peroxide is used most advantageously.

Method 5

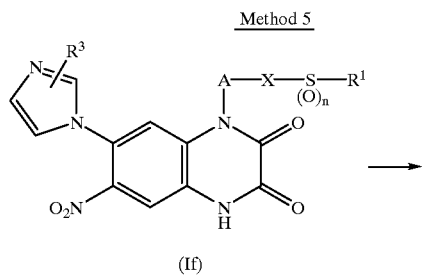

(If)

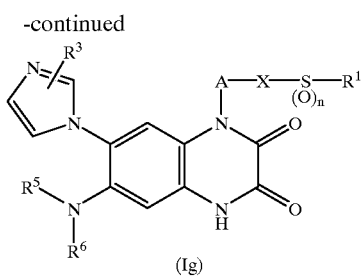

(Ig)

(In the above reaction formula, A, X, $R^1$, $R^3$ and n have the meanings described above, and $R^5$ and $R^6$ may be the same or different from each other and each represents a hydrogen atom or a lower alkyl group.)

A compound (Ig) of the present invention, which is an amine or alkylamino derivative, can be produced by carrying out reduction of its corresponding nitro compound used as the starting compound and then, if necessary, subjecting the product to N-alkylation reaction.

The reduction reaction can be effected by dissolving the compound (If) in a weak alkali aqueous solution or an appropriate organic solvent such as DMF and then carrying out hydrogenation using a catalyst such as palladium, palladium-carbon, Raney nickel or the like.

The N-alkylation reaction can be carried out in accordance with the commonly used methods, but it is advantageous to carry out the reaction using the compound (If) and a lower alkyl halide such as methyl iodide or a lower alkyl organic sulfonate such as methyl tosylate in reaction-corresponding amounts, or one of them in an excess amount, in a reaction-inert organic solvent such as DMF in the presence of a base such as sodium hydride under a temperature condition of from cooling to heating.

In this connection, in order to efficiently obtain a mono-lower alkyl compound in which either one of $R^5$ and $R^6$ is a lower alkyl group, the reaction can be carried out by introducing a protecting group for the prevention of tertiarization.

In addition, a compound (Ig) of the present invention in which either one or both of $R^5$ and $R^6$ is a lower alkyl group can be produced by subjecting a compound in which $R^2$ is a halogen atom or an organic sulfonate residue and a mono- or di-lower alkylamine to N-alkylation in the same manner.

The starting compound of each of the aforementioned production methods can be obtained easily by the methods described in Reference Examples and Examples or in accordance with the methods described in Reference examples and Examples or the aforementioned reference 1, or by modifying them.

For example, an alcohol compound (IIa) in which the side chain of $R^1$ is a hydroxy group can be produced by a method shown in the following reaction formula.

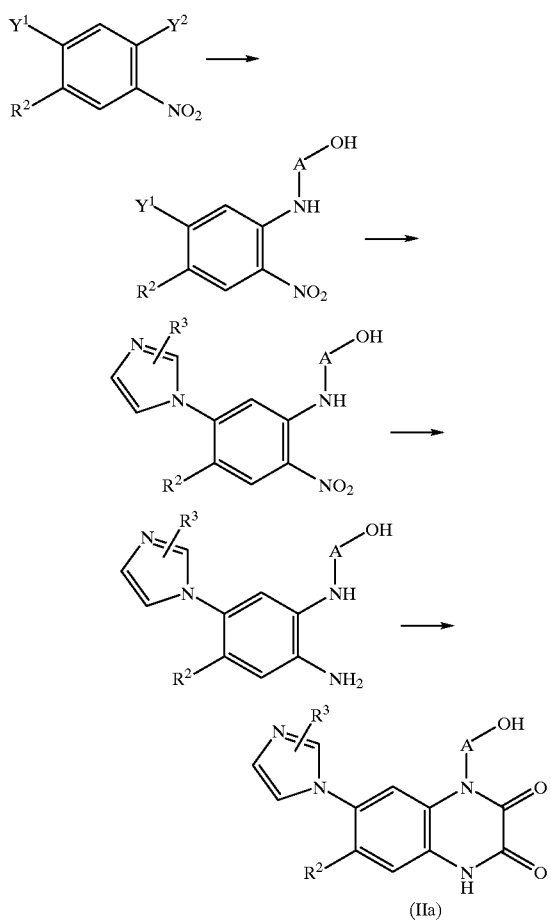

(In the above reaction formula, A, R² and R³ have the meanings described above, Y¹ means a halogen atom and Y² means the same halogen atom of Y¹ or other halogen atom having more higher reactivity.)

In this reaction route, groups other than an amino group or mono-lower alkyl groups are also desirable as R², and a compound having such groups can be obtained by optionally selecting a reaction condition such as introduction of a protecting group.

Also, a halo-compound (IV) in which the side chain of R¹ is a halogen atom and an amine compound (IIb) in which the side chain of R¹ is an amino group can be produced by a method shown in the following reaction formula.

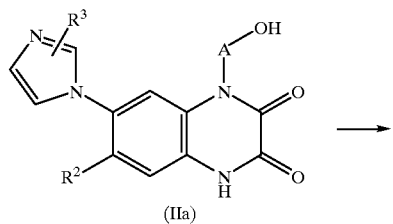

(In the above reaction formula, A, Y, R² and R³ have the meanings described above.)

In this reaction route, groups other than an amino group or mono-lower alkyl groups are also desirable as R², and a compound having such groups can be obtained by optionally selecting a reaction condition such as introduction of a protecting group.

The compound of the present invention produced in this manner is isolated in its free form or as a salt thereof. Salts of the compound of the present invention can be producing by applying usual salt formation methods to the inventive compound which is a free acid or base.

Its isolation and purification are carried out by employing extraction, concentration, evaporation, crystallization, filtration, recrystallization, various chromatographic means and the like usually used chemical techniques. For example, the sulfuric ester and sulfamine derivatives produced in the Methods 1 and 2 can be isolated and purified by adding ice water to each reaction solution to effect precipitation of crystals and then collecting the resulting crystals by filtration.

Various types of isomers can be isolated in the usual way making use of differences in physicochemical properties between isomers. For example, a racemic compound can be made into a stereochemically pure isomer by a conventional racemic resolution method [for instance, a method in which such a compound is made into its diastereomer salt with a usual optically active acid (e.g., tartaric acid) and then subjected to optical resolution]. Also, a diastereomer mixture can be separated by a general method such as fractional crystallization, chromatography or the like.

Also, an optically active compound can be produced by using an appropriate optically active material.

INDUSTRIAL APPLICABILITY

It has been confirmed that the compound of the present invention has glutamate receptor antagonisms, particularly AMPA receptor and/or NMDA-glycine receptor antagonism, and can show strong activities in kainic acid neurotoxicity inhibition action and audiogenic seizure inhibition action in DBA/2 mice.

In consequence, the compound of the present invention is an agent which, based on these functions, is particularly useful as a psychotropic agent in preventing or treating diseases such as Huntington chorea, Parkinson disease, epilepsy, Alzheimer disease, senile dementia and the like or as an anti-ischemia drug in preventing or treating neurodegeneration or mental and motor function insufficiencies after a state of cerebral ischemia, oxygen deficiency, cell death at the time of transient cardiac arrest, hypoglycemia or spasm, and is also effective for treating drug dependence and alcohol dependence.

Also, the compound of the present invention is a markedly useful compound, because it has excellent water-solubility so that it can be formulated easily as oral preparations such as tablets, capsules or parenteral preparations such as injections.

In addition, the compound of the present invention has high usability in the clinical administration as well, because it is highly soluble in blood and hardly precipitated in organs and the like.

Test Methods

The [$^3$H]-AMPA binding inhibition activity, kainic acid neurotoxicity inhibition action and audiogenic seizure inhibition action of the compound of the present invention have been confirmed in the following manner.

1) Measurement of [$^3$H]-AMPA binding inhibition activity:

A 0.5 ml portion in total volume of a reaction solution containing about 45 nM of [$^3$H]-AMPA [2-amino-3-(3-hydroxy-5-methyl-4-isoxazole)propionic acid], about 300 mg of rat cerebral membrane samples and each of the test compounds was allowed to undergo 45 minutes of the reaction on ice water. The amount of [$^3$H]-AMPA bonded to the AMPA receptor was measured by a filtration method. The portion substituted by 10 $\mu$M of quisqualic acid among the total amount of binding was defined as the amount of specific binding. Evaluation of the test compounds was carried out by calculating the ratio of binding inhibition exerted on the specific binding.

As the test compounds, the compound of Example 3, which will be described later, was used as the compound of the present invention, and a compound described as Example 1 in the aforementioned reference 1, represented by the following formula (to be referred to as comparative compound 1 hereinafter), was used as a comparative compound. In addition, a comparison was made with data of a compound represented by the following formula (to be referred to as comparative compound 2 hereinafter) which is a compound exemplified in the aforementioned reference 2 as a compound which can be produced in the same manner as the compound of Example 6 of the reference and has also been reported as a compound (compound name: ZK 200775) having excellent effects at the American Society of Neuroscience (1996).

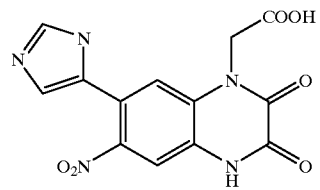

Comparative compound 1

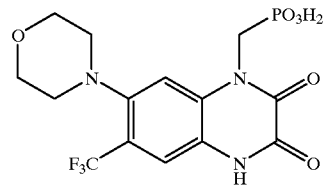

Comparative compound 2

As a result (cf. the following Table 1), it was confirmed that the compound of the present invention shows about four times higher effects than each of the comparative compound.

TABLE 1

| Compound | AMPA binding inhibition activity (IC$_{50}$, nM) |
|---|---|
| Example 3 (invention compound) | 39 |
| Comparative compound 1 | 140 |
| Comparative compound 2 | 150* |

*Data reported at the American Society of Neuroscience (1996)

2) Measurement of kainic acid neurotoxicity inhibition activity:

The action of the compound of the present invention to inhibit kainic acid neurotoxicity was examined using a primary culture system of rat fetal hippocampus neurons.

(1) Culture conditions

Hippocampus was excised from the brain of a rat of 18 to 20 days of age and treated with enzymes papain and DNase I to disperse the cells. The cells were suspended in MEM containing 10% serum and inoculated in 4×10$^5$ cells/cm$^2$ portions into wells of a 48 well plate which has been treated in advance with poly-l-lysine, and the medium was exchanged with serum-free medium 24 hours thereafter. The medium exchange was carried out twice a week. The cells cultured for 6 days or more were used in the following test.

(2) Kainic acid neurotoxicity inhibition

The neurotoxicity was expressed as the activity of lactate dehydrogenase released in the culture medium caused by cell death. Cells exposed for 24 hours to serum-free medium containing 300 $\mu$M of kainic acid were used as the control, and the action of each of the same test compounds used in the above item 1) to inhibit neuronal death caused by kainic acid was evaluated by allowing each compound to act upon the neurons for 24 hours simultaneously with 300 $\mu$M of kainic acid.

As a result (cf. the following Table 2), it was confirmed that the compound of the present invention shows about five times higher effects than the comparative compound 1.

TABLE 2

| Compound | Anti-kainic acid neurotoxicity ($IC_{50}$, μM) |
| --- | --- |
| Example 3 (invention compound) | 0.16 |
| Comparative compound 1 | 0.8 |

3) Measurement of audiogenic seizure inhibition action in DBA/2 mice

In a sound proof box, a total of 10 male mice of 21 to 28 days of age were exposed to auditory and stimulation by the sound of 12 kHz and 120 dB was applied for 1 minute or until the mice fell into a fit of convulsions. A compound to be tested (the compound of Example 3 which will be described later) was suspended in 0.5% methyl cellulose solution or dissolved in physiological saline and administered by intraperitoneal injection 15 minutes before the sound stimulus. The drug efficacy was evaluated by the presence or absence of spasm, and the minimum effective dose (MED) was calculated.

As a result, the compound of Example 3 as a compound of the present invention inhibited audiogenic seizure with a dose of 3 mg/kg.

A pharmaceutical preparation which contains one or more of the inventive compounds or salts thereof as the active ingredient is prepared making use of carriers, fillers and other additives generally used in pharmaceutical preparations.

The carriers and fillers may be either in the solid or liquid form, and their examples include lactose, magnesium stearate, starch, talc, gelatin, agar, pectin, acacia, olive oil, sesame oil, cacao butter, ethylene glycol and the like, as well as other usually used substances.

The solid composition for use in the oral administration according to the present invention is used in the form of tablets, powders, granules and the like. In such a solid composition, one or more active substances are mixed with at least one inert diluent such as lactose, mannitol, glucose, hydroxypropylcellulose, microcrystalline cellulose, starch, polyvinyl pyrrolidone or aluminum magnesium silicate. In the usual way, the composition may contain other additives than the inert diluent, such as lubricants (e.g., magnesium stearate), disintegrating agents (e.g., calcium cellulose glycolate), stabilizing agents (e.g., lactose) and solubilizing or solubilization assisting agents (e.g., glutamic acid and aspartic acid). If necessary, tablets or pills may be coated by sugar coating or with a film of a gastric or enteric substance such as sucrose, gelatin, hydroxypropylcellulose, hydroxypropylmethylcellulose phthalate or the like.

The liquid composition for oral administration includes pharmaceutically acceptable emulsions, solutions, suspensions, syrups, elixirs and the like and contains a generally used inert diluent such as purified water or ethanol. In addition to the inert diluent, this composition may also contain auxiliary agents such as a solubilizing or solubilization assisting agent, a moistening agent, a suspending agent and the like, as well as sweeteners, flavors, aromatics and antiseptics.

The injections for use in the parenteral administration include aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include propylene glycol, polyethylene glycol, plant oils (e.g., olive oil), alcohols (e.g., ethanol) and polysorbate 80 (trade name). Such a composition may further contain additive agents such as a tonicity agent, an antiseptic, a moistening agent, an emulsifying agent, a dispersing agent, a stabilizing agent (e.g., lactose) and a solubilizing or solubilization assisting agent. These compositions are sterilized by filtration through a bacteria retaining filter, blending of a germicide or irradiation. Alternatively, they may be used by firstly making into sterile solid compositions and dissolving them in sterile water or a sterile solvent for injection use prior to their use.

The administration may be carried out either by oral administration in the form of tablets, pills, capsules, granules, powders, solutions and the like or by parenteral administration in the form of intravenous and intramuscular injections, suppositories, percutaneous preparations and the like. The dose is optionally decided by taking into consideration symptoms, age, sex and the like of each patient to be treated, but the compound is generally administered by oral administration in a dose of from 1 to 1,000 mg, preferably from 50 to 200 mg, per day per adult, once a day or by dividing the daily dose into several doses per day, by intravenous injection in a dose of from 1 to 500 mg per day per adult once a day or by dividing the daily dose into several doses per day, or by intravenous continuous injection within the range of from 1 to 24 hours per day. Since the dose varies under various conditions as described above, a smaller dose than the above range may be sufficient enough in some cases.

BEST MODE OD CARRYING OUT THE INVENTION

Next, examples of the present invention are given below by way of illustration and not by way of limitation. In this connection, examples of the production of main starting compounds to be used in the Examples are described as reference examples.

REFERENCE EXAMPLE 1

2,4-Difluoronitrobenzene (4 g) and 2-aminoethanol (3.1 ml) were allowed to react with each other in isopropanol (30 ml) at room temperature, and, a whole day and night thereafter, water was added to the reaction solution and the thus formed crystals were collected by filtration. The resulting 2-(5-fluoro-2-nitroanilino)ethanol (3.95 g) was allowed to react with imidazole (5.3 g) in DMSO (4 ml) at 80° C. for a whole day and night. Water was added to the reaction solution, and the thus formed crystals were collected by filtration. The resulting 2-[5-(1H-imidazol-1-yl)-2-nitroanilino]ethanol (4.3 g) was subjected to reduction in ethanol (60 ml) in the presence of 10% palladium-carbon (0.4 g). The catalyst was removed by filtration, the resulting reaction solution was concentrated and then the resulting diamine compound was heated under reflux for 4 hours in oxalic acid (4.7 g) and 4 N hydrochloric acid (30 ml). By cooling the reaction solution with ice, 1-(2-hydroxyethyl)-7-(1H-imidazol-1-yl)-2,3-(1H,4H)-quinoxalinedione hydrochloride was obtained (77% in yield through four steps).

Mass spectrometry data (m/z): 273 (M+H)$^+$ Nuclear magnetic resonance spectrum (DMSO-$d_6$, TMS internal standard);

δ: 3.71 (m, 2 H), 4.31 (m, 2 H), 7.38 (d, 1 H), 7.58 (dd, 1 H), 7.94 (t, 1 H), 7.97 (d, 1 H), 8.36 (t, 1 H), 9.87 (s, 1 H), 12.34 (s, 1 H).

REFERENCE EXAMPLE 2

1-(3-Hydroxypropyl)-7-(1H-imidazol-1-yl)-2,3(1H,4H)-quinoxalinedione hydrochloride was obtained in the same manner as described in Reference Example 1, except that 3-aminopropanol was used instead of 2-aminoethanol. High performance liquid chromatography Developing system (0.1 M ammonium acetate-methanol=1:1) Retention time (1 ml/1 min) 2.41 minutes.

REFERENCE EXAMPLE 3

2,4-Difluoronitrobenzene (7.1 g) and 4-aminobutanol (8.5 ml) were allowed to react with each other in isopropanol (40 ml) at room temperature, and, 5 hours thereafter, water was added to the reaction solution and the thus formed crystals were collected by filtration. The resulting 4-(5-fluoro-2-nitroanilino)butanol (3.5 g) was allowed to react with imidazole (4.1 g) in DMSO (3.5 ml) at 80° C. for 24 hours, water was added to the resulting reaction solution, and then the thus formed crystals were collected by filtration. The resulting 4-[5-(1H-imidazol-1-yl)-2-nitroanilino]butanol (4 g) was subjected to reduction in ethanol (10 ml) in the presence of 10% palladium-carbon (0.7 g). The catalyst was removed by filtration, the resulting reaction solution was concentrated, and then the resulting diamine compound with oxalic acid (4.0 g) was heated under reflux for 4 hours in 4 N hydrochloric acid. By cooling the reaction solution with ice, 3.2 g of 1-(4-hydroxybutyl)-7-(1H-imidazol-1-yl)-2,3 (1H,4H)-quinoxalinedione hydrochloride was obtained (55% in yield through 4 steps).

Mass spectrometry data (m/z): 301 (M+H)$^+$ Nuclear magnetic resonance spectrum (DMSO-d$_6$, TMS internal standard);

δ: 1.53 (m, 2 H), 1.70 (m, 2 H), 3.45 (t, 2 H), 4.20 (t, 2 H), 7.41 (d, 1 H), 7.59 (dd, 1 H), 7.90 (d, 1 H), 7.93 (t, 1 H), 8.31 (t, 1 H), 9.80 (s, 1 H), 12.36 (s, 1 H).

REFERENCE EXAMPLE 4

1-(5-Hydroxypentyl)-7-(1H-imidazol-1-yl)-2,3(1H,4H)-quinoxalinedione hydrochloride was obtained in the same manner as described in Reference Example 1, except that 5-aminopentanol was used in stead of 2-aminoethanol.

REFERENCE EXAMPLE 5

1-(6-Hydroxyhexyl)-7-(1H-imidazol-1-yl)-2,3(1H,4H)-quinoxalinedione hydrochloride was obtained in the same manner as described in Reference Example 1, except that 6-aminohexanol was used in stead of 2-aminoethanol.

Mass spectrometry data (m/z): 329 (M+H)$^+$ Nuclear magnetic resonance spectrum (DMSO-d$_6$, TMS internal standard);

δ: 1.40 (m, 5 H), 1.65 (m, 3 H), 3.38 (t, 1 H), 4.19 (m, 3 H), 7.41 (d, 1 H), 7.59 (dd, 1 H), 7.78 (s, 1 H), 7.95 (s, 1 H), 8.33 (s, 1 H), 9.85 (s, 1 H), 12.37 (s, 1 H).

REFERENCE EXAMPLE 6

With ice-cooling, 4-aminobutanol (0.72 g) dissolved in ethanol (5 ml) was added dropwise to ethanol (10 ml) solution of 1,5-difluoro-2-nitro-4-trifluoromethylbenzene (0.73 g), and the reaction was carried out overnight at room temperature. The reaction solution was concentrated and the resulting residue was purified by a silica gel column chromatography (n-hexane:ethyl acetate=1:1) to give 4-(5-fluoro-2-nitro-4-trifluoromethylanilino)butanol (0.76 g). The resulting anilinobutanol (0.66 g) and imidazole (1.5 g) were allowed to react with each other in DMF (10 ml) at 140° C. for 1 hour, the reaction solution was concentrated and then the resulting residue was purified by a silica gel column chromatography (chloroform:methanol =15:1) to give 4-[5-(1H-imidazol-1-yl)-2-nitro-4-trifluoromethylanilino)butanol (0.68 g).

Mass spectrometry data (m/z) EI-MS: 344 (M)$^+$ Nuclear magnetic resonance spectrum (DMSO-d$_6$, TMS internal standard);

δ: 1.63–1.99 (m, 4 H), 3.39 (q, 2 H), 3.75 (t, 2 H), 6.84 (s, 1 H), 7.16 (s, 1 H), 7.21 (s, 1 H), 7.66 (s, 1 H), 8.39 (brs, 1 H), 8.64 (s, 1 H).

REFERENCE EXAMPLE 7

1,4-Diaminobutane (4.19 g) was dissolved in tetrahydrofuran (THF: 300 ml) to which, at −10° C., was subsequently added dropwise 2,4-difluoronitrobenzene (3.00 g) dissolved in THF (100 ml). The reaction solution was warmed up to room temperature, stirred for 3 hours and then mixed with di-tert-butyl dicarbonate (8.22 g). The reaction solution was further stirred overnight, the thus formed insoluble matter was separated by filtration, the resulting filtrate was concentrated, and a mixed solution (150 ml) of n-hexane:ethyl acetate=1:2 was added to the residue. The thus formed insoluble matter was again separated by filtration and then the filtrate was concentrated under a reduced pressure. The resulting yellow solid was purified by a silica gel column chromatography (n-hexane:ethyl acetate=1:2) to give N-(4-tert-butoxycarbonylaminobutyl)-5-fluoro-2-nitroaniline (4.67 g). The resulting aniline compound (3.20 g) and imidazole (4.00 g) were dissolved in DMSO (50 ml). The solution was stirred at 150° C. for 4 hours, spontaneously cooled down to room temperature and, after addition of water (500 ml), extracted with ethyl acetate and then washed with water. The organic layer was dried over anhydrous sodium sulfate and then concentrated, and the resulting solid substance was washed with water and dried under a reduced pressure to give N-(4-tert-butoxycarbonylaminobutyl)-5-(1H-imidazol-1-yl)-2-nitroaniline (3.13 g). In an atmosphere of hydrogen, the thus formed product (3.00 g) was subjected to 4 hours of reduction in ethanol under ordinary pressure, using palladium-carbon as the catalyst. The reaction solution was filtered and concentrated under a reduced pressure. Then, oxalic acid (2.16 g) and 4 N hydrochloric acid (40 ml) were added to the residue, followed by heating under reflux for 8 hours. The reaction solution was filtered, and the resulting filtrate was concentrated to about half of the volume. The thus precipitated crystals were collected by filtration and dried under a reduced pressure to give 1-(4-aminobutyl)-7-(1H-imidazol-1-yl)-2,3(1H,4H)-quinoxalinedione dihydrochloride (2.87 g).

Mass spectrometry data (m/z) FAB-MS: 300 (M+H)$^+$ Nuclear magnetic resonance spectrum (DMSO-d$_6$, TMS internal standard);

δ: 1.67 (qu, 2 H), 1.78 (qu, 2 H), 2.88 (q, 2 H), 4.24 (t, 2 H), 7.40 (d, 1 H), 7.57 (dd, 1 H), 7.79 (s, 2 H), 8.03 (brs, 2 H), 8.26 (s, 1 H), 9.62 (s, 1 H) , 12.37 (brs, 1 H).

REFERENCE EXAMPLE 8

With ice-cooling, 1-(4-aminobutyl)-7-(1H-imidazol-1-yl)-2,3(1H,4H)-quinoxalinedione dihydrochloride (1.00 g) was dissolved in concentrated sulfuric acid (10 ml) to which was subsequently added dropwise fuming nitric acid (94 μl). The reaction solution was gradually warmed up to room temperature and stirred overnight. Ice water was added to the reaction solution, followed by neutralization using 15% sodium hydroxide aqueous solution. The thus precipitated solid was collected by filtration and dried to give 1-(4-aminobutyl)-7-(1H-imidazol-1-yl)-6-nitro-2,3(1H,4H)-quinoxalinedione (0.40 g).

Mass spectrometry data (m/z) FAB-MS: 345 (M+H)$^+$ Nuclear magnetic resonance spectrum (DMSO-d$_6$, TMS internal standard);

δ: 1.56 (m, 2 H), 1.65 (m, 2 H), 2.67 (m, 2 H), 4.15 (t, 2 H), 7.07 (s, 1 H), 7.36 (s, 1 H), 7.40 (s, 1 H), 7.66 (t, 1 H), 7.90 (s, 1 H).

REFERENCE EXAMPLE 9

At room temperature, 4-[5-(1H-imidazol-1-yl)-2-nitro-4-trifluoromethylanilino)butanol (5.79 g) synthesized in Reference Example 6 was subjected to reduction in ethanol at ordinary temperature using 10% palladium-carbon as the catalyst, thereby converting it into 4-[2-amino-5-(1H-imidazol-1-yl)-4-trifluoromethylanilino)butanol which was subsequently dissolved in 48% hydrobromic acid aqueous solution (50 ml). Then, oxalic acid (2.27 g) was added, followed by heating overnight under reflux. The reaction solution was concentrated under a reduced pressure, and addition of water to the resulting residue followed by concentration was repeated several times. When the residue became a water-insoluble solid, this was collected by filtration, washed with water and then dried under a reduced pressure, and the resulting crude product was recrystallized from DMF-water to give 1-(4-bromobutyl)-7-(1H-imidazol-1-yl)-6-trifluoromethyl-2,3(1H,4H)-quinoxalinedione hydrobromide (2.46 g). The resulting bromobutylquinoxalinedione (2.46 g) and tetra-n-butylammonium bromide (0.15 g) were dissolved in a two layer system solution of chloroform (50 ml), water (50 ml) and DMF (25 ml), and the solution was adjusted to pH 7 by adding 1 N sodium hydroxide. Then, sodium azide (3.12 g) was added, followed by heating overnight under reflux. The organic layer was separated from the reaction solution, washed with water, dried over anhydrous sodium sulfate and then concentrated under a reduced pressure. As the remaining solid substance, 1-(4-azidobutyl)-7-(1H-imidazol-1-yl)-6-trifluoromethyl-2,3(1H,4H)-quinoxalinedione (1.61 g) was obtained. Next, in an atmosphere of hydrogen, the resulting azidobutylquinoxalinedione (1.30 g) was subjected to reduction under normal pressure in DMF (65 ml) using palladium-carbon as the catalyst. The reaction solution was filtered to collect insoluble matter including the catalyst. This was dissolved in heated DMF, filtered during hot condition and then recrystallized to give 1-(4-aminobutyl)-7-(1H-imidazol-1-yl)-6-trifluoromethyl-2,3(1H,4H)-quinoxalinedione (0.82 g).

Mass spectrometry data (m/z) FAB-MS: 368 (M+H)$^+$ Nuclear magnetic resonance spectrum (DMSO-d$_6$, TMS internal standard);

δ: 1.51 (qu, 2 H), 1.63 (qu, 2 H), 2.74 (m, 2 H), 4.11 (t, 2 H), 7.06 (s, 1 H), 7.36 (s, 1 H), 7.38 (s, 1 H), 7.40 (s, 1 H), 7.82 (s, 1 H).

REFERENCE EXAMPLE 10

With ice-cooling, 1,5-difluoro-2-nitro-4-trifluoromethylbenzene (1.50 g) and 3-aminobenzyl alcohol (1.62 g) were dissolved in ethanol (50 ml) and subjected to 3 hours of the reaction at room temperature. The reaction solution was concentrated and the resulting residue was purified by a silica gel column chromatography (chloroform:methanol=100:1) to give [3-(5-fluoro-2-nitro-4-trifluoromethylanilino)phenyl]methanol (1.93 g). The resulting anilinophenylmethanol (1.75 g) and imidazole (3.61 g) were allowed to react with each other in DMF (50 ml) at 140° C. for 30 minutes, and the resulting reaction solution was spontaneously cooled down to room temperature. Then, saturated sodium chloride aqueous solution (150 ml) was added. The thus formed orange solid was collected by filtration, washed with water and then dried under a reduced pressure. The resulting crude crystals were purified by a silica gel column chromatography (chloroform:methanol=10:1) to give [3-[5-(1H-imidazol-1-yl)-2-nitro-4-trifluoromethylanilino]phenyl]methanol (1.46 g). In an atmosphere of hydrogen, the thus formed product (1.37 g) in methanol was subjected to reduction under ordinary pressure using palladium-carbon as the catalyst. The reaction solution was filtered and concentrated under a reduced pressure to give amorphous residue. Then, oxalic acid (0.13 g) and 1 N hydrochloric acid aqueous solution (10 ml) were added, followed by heating at 100° C. for 15 hours. When the reaction solution was concentrated to about half in volume, the thus formed crystals were collected by filtration, washed with ethyl acetate and then dried under a reduced pressure to give 1-(3-hydroxymethylphenyl)-7-(1H-imidazol-1-yl)-6-trifluoromethyl-2,3(1H,4H)-quinoxalinedione hydrochloride (1.20 g).

Mass spectrometry data (m/z) FAB-MS: 403 (M+H)$^+$ Nuclear magnetic resonance spectrum (DMSO-d$_6$, TMS internal standard);

δ: 4.57 (s, 2 H), 6.85 (s, 1 H), 7.23 (d, 1 H), 7.34 (s, 1 H), 7.45 (d, 1 H), 7.55 (d, 1 H), 7.73 (s, 1 H), 7.84 (s, 1 H), 7.85 (s, 1 H), 9.28 (s, 1 H), 12.69 (brs, 1 H).

EXAMPLE 1

An 1 g portion of 1-(2-hydroxyethyl)-7-(1H-imidazol-1-yl)-2,3(1H,4H)-quinoxalinedione hydrochloride was dissolved in 5 ml of concentrated sulfuric acid with ice-cooling, and then 0.36 g of potassium nitrate was added thereto. The reaction solution was gradually warmed up to room temperature to carry out 5 hours of the reaction. When ice water was added to the reaction solution, crystals were precipitated soon thereafter, and they were collected by filtration and dried to give 2-[2,3-dioxo-7-(1H-imidazol-1-yl)-6-nitro-1,2,3,4-tetrahydroquinoxalin-1-yl]ethanesulfate (0.66 g).

Mass spectrometry data (m/z): 398 (M+H)$^+$ Melting point: 300° C. or more Nuclear magnetic resonance spectrum (DMSO-d$_6$, TMS internal standard);

δ: 4.06 (d, 2 H), 4.39 (d, 2 H), 7.93 (s, 1 H), 8.01 (s, 1 H), 8.15 (s, 1 H), 8.25 (s, 1 H), 9.53 (s, 1 H), 12.50 (s, 1 H).

EXAMPLE 2

Using 0.5 g of 1-(3-hydroxypropyl)-7-(1H-imidazol-1-yl)-2,3(1H,4H)-quinoxalinedione hydrochloride, 2.5 ml of sulfuric acid and 173 mg of potassium nitrate, the reaction of Example 1 was repeated to give 3-[2,3-dioxo-7-(1H-imidazol-1-yl)-6-nitro-1,2,3,4-tetrahydroquinoxalin-1-yl]propanesulfate (218 mg).

Mass spectrometry data (m/z): 412 (M+H)$^+$ Melting point: 300° C. or more Nuclear magnetic resonance spectrum (DMSO-d$_6$, TMS internal standard);

δ: 1.94 (m, 2 H), 3.79 (t, 2 H), 4.15 (t, 2 H), 7.89 (s, 1 H), 7.97 (s, 1 H), 8.08 (s, 1 H), 8.10 (s, 1 H), 9.56 (s, 1 H), 12.47 (s, 1 H).

EXAMPLE 3

A 3.08 g portion of 1-(4-hydroxybutyl-7-(1H-imidazol-1-yl)-2,3(1H,4H)-quinoxalinedione hydrochloride was dissolved in 15 ml of concentrated sulfuric acid with ice-cooling, and then 1.5 g of potassium nitrate was added thereto. The reaction solution was gradually warmed up to room temperature to carry out a total of 3.5 hours of the reaction. When ice water was added to the reaction solution, crystals were precipitated soon thereafter, and they were collected by filtration and dried to give 4-[2,3-dioxo-7-(1H-imidazol-1-yl)-6-nitro-1,2,3,4-tetrahydroquinoxalin-1-yl] butanesulfate (2.45 g).

Mass spectrometry data (m/z): 426 (M+H)$^+$ Melting point: 300° C. or more Nuclear magnetic resonance spectrum (DMSO-d$_6$, TMS internal standard);

δ: 1.63 (m, 2 H), 1.69 (m, 2 H), 3.76 (t, 2 H), 4.10 (m, 2 H), 7.88 (s, 1 H), 7.99 (s, 1 H), 8.04 (s, 1 H), 8.10 (s, 1 H), 9.48 (s, 1 H), 12.47 (s, 1 H).

EXAMPLE 4

A 0.7 g portion of 1-(5-hydroxypentyl)-7-(1H-imidazol-1-yl)-2,3(1H,4H)-quinoxalinedione hydrochloride was dissolved in 3.5 ml of concentrated sulfuric acid with ice-cooling, and then 0.22 g of potassium nitrate was added thereto. The reaction solution was gradually warmed up to room temperature to carry out a total of 1 hour of the reaction. When ice water was added to the reaction solution, crystals were precipitated soon thereafter, and they were collected by filtration and dried to give 5-[2,3-dioxo-7-(1H-imidazol- 1-yl)-6-nitro-1,2,3,4-tetrahydroquinoxalin-1-yl] pentanesulfate (348 mg).

Mass spectrometry data (m/z): 440 (M+H)$^+$ Melting point: 290° C. decomp. Nuclear magnetic resonance spectrum (DMSO-d$_6$, TMS internal standard);

δ: 1.41 (m, 2 H), 1.53 (m, 1 H), 1.66 (m, 3 H), 4.08 (m, 3 H), 4.19 (m, 1 H), 7.84 (s, 1 H), 7.94 (s, 1 H), 8.04 (s, 1 H), 8.10 (s, 1 H), 9.44 (s, 1 H), 12.47 (s, 1 H).

EXAMPLE 5

A 1.0 g portion of 1-(6-hydroxyhexyl)-7-(1H-imidazol-1-yl)-2,3(1H,4H)-quinoxalinedione hydrochloride was dissolved in 5 ml of concentrated sulfuric acid with ice-cooling, and then 0.3 g of potassium nitrate was added thereto. The reaction solution was gradually warmed up to room temperature to carry out 1 hour in total of the reaction. When ice water was added to the reaction solution, crystals were precipitated soon thereafter, and they were collected by filtration and dried to give 6-[2,3-dioxo-7-(1H-imidazol-1-yl)-6-nitro-1,2,3,4-tetrahydroquinoxalin-1-yl]hexanesulfate (495 mg).

Mass spectrometry data (m/z): 454 (M+H)$^+$ Melting point: 262° C. decomp. Nuclear magnetic resonance spectrum (DMSO-d$_6$, TMS internal standard)

δ: 1.35 (m, 5 H), 1.49 (m, 1 H), 1.63 (m, 2 H), 4.08 (m, 3 H), 4.20 (m, 1 H), 7.83 (s, 1 H), 7.92 (s, 1 H), 8.00 (s, 1 H), 8.09 (s, 1 H), 9.36 (s, 1 H), 12.46 (s, 1 H).

EXAMPLE 6

In an atmosphere of hydrogen, 4-[5-(1H-imidazol-1-yl)-2-nitro-4-trifluoromethylanilino)butanol (0.68 g) synthesized in Reference Example 6 was subjected to reduction in ethanol (20 ml) under ordinary pressure using palladium-carbon as the catalyst, and the reaction solution was filtered and concentrated. The resulting 4-[2-amino-5-(1H-imidazol-1-yl)-4-trifluoromethylanilino)butanol as the residue and oxalic acid (0.20 g) were dissolved in 4 N hydrochloric acid aqueous solution (20 ml) and heated under reflux for 5 hours. The reaction solution was then concentrated under a reduced pressure. The resulting residue was dissolved in a small amount of water and neutralized with 1 N sodium hydroxide aqueous solution. The thus formed gummy material was washed several times with water and ethanol by repeating decantation. This was dried under a reduced pressure to give 1-(4-hydroxybutyl)-7-(1H-imidazol-1-yl)-6-trifluoromethyl-2,3(1H,4H)-quinoxalinedione (0.57 g) in the solid form. The resulting quinoxalinedione compound (0.57 g) was dissolved in 5 ml of concentrated sulfuric acid with ice-cooling, and the reaction solution was gradually warmed up to room temperature to carry out 1 hour in total of the reaction. When ice water was added to the reaction solution, crystals were precipitated soon thereafter, and they were collected by filtration and dried to give 4-[2,3-dioxo-7-(1H-imidazol-1-yl)-6-trifluoromethyl-1,2,3,4-tetrahydroquinoxalin-1-yl] butanesulfate (82 mg).

Mass spectrometry data (m/z) FAB-MS: 449 (M+H)$^+$ Melting point: >300° C. Nuclear magnetic resonance spectrum (DMSO-d$_6$, TMS internal standard);

δ: 1.60–1.70 (m, 4 H), 3.75 (t, 2 H), 4.09 (t, 2 H), 7.65 (s, 1 H), 7.90 (s, 1 H), 8.02 (s, 1 H), 8.06 (s, 1 H), 9.52 (s, 1 H), 12.41 (brs, 1 H).

EXAMPLE 7

1-(4-Aminobutyl)-7-(1H-imidazol-1-yl)-6-nitro-2,3(1H, 4H)-quinoxalinedione (0.20 g) synthesized in Reference Example 8 was suspended in triethylamine (10 ml) Sulfur trioxide-pyridine complex (0.46 g) was added to the suspension, followed by heating under reflux for 1 hour. After spontaneous cooling to room temperature, the supernatant fluid was removed by decantation to give oily residue. This is dissolved in ethanol and then concentrated under a reduced pressure. By repeating this step, a light brown solid starts to form by the addition of ethanol. The thus formed precipitate was collected by filtration and suspended again in ethanol, and the suspension was adjusted to pH 8 by adding 1 N sodium hydroxide aqueous solution and then filtered. The resulting filtrate was concentrated and the resulting residue was repeatedly washed with ether and ethanol and then dried under a reduced pressure to give solid form of 4-[2,3-dioxo-7-(1H-imidazol-1-yl)-6-nitro-1,2,3,4-tetrahydroquinoxalin-1-yl]butylsulfamic acid sodium salt (62 mg).

Mass spectrometry data (m/z) FAB-MS: 447 (M+Na)$^+$ Melting point: >260° C. (decomp.) Nuclear magnetic resonance spectrum (DMSO-d$_6$, TMS internal standard);

δ: 1.45 (qu, 2 H), 1.62 (m, 2 H), 2.72 (t, 2 H), 4.13 (t, 2 H), 7.08 (s, 1 H), 7.45 (s, 1 H), 7.67 (s, 1 H), 7.92 (s, 1 H), 7.94 (s, 1 H), 12.41 (brs, 1 H).

EXAMPLE 8

1-(4-Aminobutyl)-7-(1H-imidazol-1-yl)-6-trifluoromethyl-2,3(1H,4H)-quinoxalinedione (0.20 g) synthesized in Reference Example 9 was suspended in triethylamine (10 ml), and the suspension. Sulfur trioxide-pyridine complex (0.86 g) was added to the suspension, followed by heating under reflux for 1 hour. After spontaneous cooling to room temperature, the supernatant fluid was removed by decantation to give gummy residue. The resulting residue was repeatedly washed with an ethanol-ether mixed solution and dissolved in ethanol, the insoluble matter was removed by filtration and then the resulting filtrate was allowed to stand overnight. The thus precipitated white crystals were collected by filtration and dried under a reduced pressure to give 4-[2,3-dioxo-7-(1H-imidazol-1-yl)-6-trifluoromethyl-1,2,3,4-tetrahydroquinoxalin-1-yl]butylsulfamic acid (36 mg).

Mass spectrometry data (m/z) FAB-MS: 448 (M+H)$^+$ Melting point: 248–250° C. Nuclear magnetic resonance spectrum (DMSO-d$_6$, TMS internal standard);

δ: 1.63 (m, 4 H), 3.00 (t, 2 H), 4.14 (t, 2 H), 7.22 (s, 1 H), 7.49 (s, 1 H), 7.62 (s, 1 H), 7.73 (s, 1 H), 8.08 (s, 1 H), 12.37 (brs, 1 H).

EXAMPLE 9

1-(4-Bromobutyl)-7-(1H-imidazol-1-yl)-6-trifluoromethyl-2,3(1H,4H)-quinoxalinedione hydrobromide (0.50 g) synthesized as an intermediate in Reference Example 9, potassium carbonate (0.15 g) and 3-mercapto-1,2,4-triazole (0.12 g) were dissolved in DMF (10 ml) and heated at 100° C. for 2 hours under reflux. The reaction solution was spontaneously cooled to room temperature, the thus formed insoluble matter was filtered, 4 N hydrochloric acid/ethyl acetate solution (2 ml) was added to the filtrate, the thus formed precipitate was filtered and then the filtrate was concentrated under a reduced pressure. Ethanol was added to the resulting syrupy residue, the thus formed precipitate was filtered and then the filtrate was concentrated. A mixed solution of ethanol and ethyl acetate was added to the residue, and then the thus formed crystals were collected by filtration and dried under a reduced pressure to give 7-(1H-imidazol-1-yl)-1-[4-(1H-1,2,4-triazolo-3-yl)thiobutyl]-6-trifluoromethyl-2,3(1H,4H)-quinoxalinedione hydrochloride (0.16 g).

Mass spectrometry data (m/z) FAB-MS: 452 (M+H)$^+$ Melting point: 195–202° C. Nuclear magnetic resonance spectrum (DMSO-d$_6$, TMS internal standard);

δ: 1.49 (m, 4 H), 3.12 (t, 2 H), 4.09 (t, 2 H), 7.74 (s, 1 H), 7.96 (t, 1 H), 8.03 (s, 1 H), 8.07 (s, 1 H), 8.41 (s, 1 H), 9.62 (s, 1 H), 12.54 (brs, 1 H).

EXAMPLE 10

7-(1H-Imidazol-1-yl)-1-[4-(1H-1,2,4-triazolo-3-yl)thiobutyl]-6-trifluoromethyl-2,3(1H,4H)-quinoxalinedione hydrochloride (84 mg) synthesized in Example 9 was dissolved in a mixed solution of 30% hydrogen peroxide aqueous solution (5 ml) and acetic acid (5 ml) and heated overnight under reflux. The reaction solution was concentrated, ethanol and ethyl acetate were added to the syrupy residue, followed by concentration. The resulting solid residue was washed with ethyl acetate and dried under a reduced pressure to give 7-(1H-imidazol-1-yl)-1-[4-(1H-1,2,4-triazol-3-ylsulfonyl)butyl]-6-trifluoromethyl-2,3(1H,4H)-quinoxalinedione hydrochloride (37 mg).

Mass spectrometry data (m/z) FAB-MS: 484 (M+H)$^+$ Melting point: amorphous Nuclear magnetic resonance spectrum (DMSO-d$_6$, TMS internal standard);

δ: 1.73 (m, 4 H), 3.48 (m, 2 H), 4.08 (brt, 2 H), 7.13 (s, 1 H), 7.26 (t, 1 H), 7.40 (s, 1 H), 7.72 (s, 1 H), 7.93 (s, 1 H), 8.88 (s, 1 H), 12.51 (brs, 1 H).

EXAMPLE 11

1-(3-Hydroxymethylphenyl)-7-(1H-imidazol-1-yl)-6-trifluoromethyl-2,3(1H,4H)-quinoxalinedione hydrochloride (0.60 g) synthesized in Reference Example 10 was dissolved in concentrated sulfuric acid (2 ml) and stirred at room temperature for 30 minutes. By purifying the reaction solution by an HP-20 column chromatography (methanol-water), 3-[2,3-dioxo-7-(1H-imidazol-1-yl)-6-trifluoromethyl-1,2,3,4-tetrahydroquinoxalin-1-yl benzylsulfate (30 mg) was obtained.

Mass spectrometry data (m/z) FAB-MS: 483 (M+H)$^+$ Melting point: >300° C. Nuclear magnetic resonance spectrum (DMSO-d$_6$, TMS internal standard);

δ: 4.84 (s, 2 H), 6.77 (s, 1 H), 7.27 (d, 1 H), 7.39 (s, 1 H), 7.48 (d, 1 H), 7.57 (t, 1 H), 7.69 (s, 3 H), 8.90 (s, 1 H), 12.47 (brs, 1 H).

EXAMPLE 12

1-(4-Aminobutyl)-7-(1H-imidazol-1-yl)-2,3(1H,4H)-quinoxalinedione dihydrochloride (1.00 g) synthesized in Reference Example 7 was suspended in triethylamine (50 ml). Sulfur trioxide-pyridine complex (4.30 g) was added to the suspension, followed by heating under reflux for 2 hours. After spontaneous cooling to room temperature, the supernatant fluid was removed by decantation to give gummy residue. The resulting residue was repeatedly washed with an ethanol-ether mixed solution and then dissolved in ethanol, and the solution was adjusted to pH 8 by adding 1 N sodium hydroxide aqueous solution. The thus precipitated insoluble matter was collected by filtration, repeatedly washed with an ethanol-ether mixed solution and then dried under a reduced pressure to give 4-[2,3-dioxo-7-(1H-imidazol-1-yl)-1,2,3,4-tetrahydroquinoxalin-1-yl]butylsulfamic acid sodium salt (39 mg).

Mass spectrometry data (m/z) FAB-MS: 402 (M+Na)$^+$ Melting point: 227–236° C. Nuclear magnetic resonance spectrum (DMSO-d$_6$, TMS internal standard);

δ: 1.50 (qu, 2 H), 1.66 (qu, 2 H), 2.76 (m, 2 H), 4.19 (m, 2 H), 7.10 (s, 1 H), 7.27 (d, 1 H), 7.43 (dd, 1 H), 7.57 (d, 1 H), 7.83 (s, 1 H), 8.29 (s, 1 H), 12.08 (brs, 1 H).

Chemical structures of the compounds obtained in the Examples are shown in the following Tables 3 and 4.

TABLE 3

| Example No. | Chemical Structure |
|---|---|
| 1 | (imidazolyl-quinoxalinedione with 2-carbon chain-OSO$_3$H; O$_2$N substituent) |
| 2 | (imidazolyl-quinoxalinedione with 3-carbon chain-OSO$_3$H; O$_2$N substituent) |
| 3 | (imidazolyl-quinoxalinedione with 4-carbon chain-OSO$_3$H; O$_2$N substituent) |
| 4 | (imidazolyl-quinoxalinedione with 5-carbon chain-OSO$_3$H; O$_2$N substituent) |

TABLE 3-continued

| Example No. | Chemical Structure |
|---|---|
| 5 | (imidazolyl-quinoxalinedione with nitro and hexyl-OSO3H chain) |
| 6 | (imidazolyl-quinoxalinedione with CF3 and butyl-OSO3H chain) |

TABLE 4

| Example No. | Chemical Structure |
|---|---|
| 7 | (imidazolyl-quinoxalinedione with O2N and butyl-NHSO3Na chain) |
| 8 | (imidazolyl-quinoxalinedione with CF3 and butyl-NHSO3H chain) |
| 9 | (imidazolyl-quinoxalinedione with CF3 and butyl-S-triazole chain, ·HCl) |
| 10 | (imidazolyl-quinoxalinedione with CF3 and butyl-SO2-triazole chain, ·HCl) |
| 11 | (imidazolyl-quinoxalinedione with CF3 and benzyl-OSO3H substituent) |
| 12 | (imidazolyl-quinoxalinedione with butyl-NHSO3Na chain) |

The compounds shown in the following can be produced easily in the same manner as the aforementioned production methods and the methods described in Examples or by applying to these methods slight modifications which are obvious to those skilled in the art.

4-[6-Cyano-2,3-dioxo-7-(1H-imidazol-1-yl)-1,2,3,4-tetrahydroquinoxalin-1-yl]butanesulfate.

4-[2,3-Dioxo-7-(1H-imidazol-1-yl)-6-methylamino-1,2,3,4-tetrahydroquinoxalin-1-yl]butanesulfate.

4-[6-Dimethylamino-2,3-dioxo-7-(1H-imidazol-1-yl)-1,2,3,4-tetrahydroquinoxalin-1-yl]butanesulfate.

4-[6-Chloro-2,3-dioxo-7-(1H-imidazol-1-yl)-1,2,3,4-tetrahydroquinoxalin-1-yl]butanesulfate.

4-[6-Bromo-2,3-dioxo-7-(1H-imidazol-1-yl)-1,2,3,4-tetrahydroquinoxalin-1-yl]butanesulfate.

2-[2,3-Dioxo-7-(1H-imidazol-1-yl)-6-trifluoromethyl-1,2,3,4-tetrahydroquinoxalin-1-yl]phenetyl-2-sulfate.

4-[2,3-Dioxo-7-(4-methyl-1H-imidazol-1-yl)-6-nitro-1,2,3,4-tetrahydroquinoxalin-1-yl]-butanesulfate.

FORMULATION EXAMPLE

Next, a formulation example is described as a pharmaceutical preparation of the compound of the present invention.

| Freeze-dried preparation In one vial | |
|---|---|
| Compound of Example | 50 mg (0.5%) |
| Citric acid | 210 mg (2.1%) |
| D-Mannitol | 100 mg (1.0%) |
| | 10 mg |

A 5 g portion of a compound of Example, 21 g of citric acid and 10 g of D-mannitol were dissolved in that order in 800 ml of water, and the total volume was adjusted to 1,000 ml by adding water.

The thus prepared solution was aseptically filtered, dispensed in 10 ml portions into brown vials and then freeze-dried to be used as injections by re-dissolving them prior to use.

We claim:

1. An imidazole-substituted quinoxalinedione compound represented by the following formula (I)

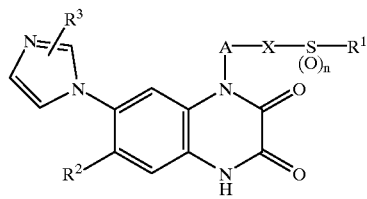

wherein each symbol has the following meaning:

A: a group represented by a formula $(CH_2)_m$ or a group represented by a formula Ph—$(CH_2)_p$ (Ph: a phenyl group), X: an oxygen atom or a group represented by a formula $NR^4$, $R^1$: a hydrogen atom, a hydroxyl group or a triazolyl group, with the proviso that X may be a bond when $R^1$ is a triazolyl group, $R^2$: a hydrogen atom, a nitro group, a halogeno-lower alkyl group, a cyano group, an amino group, a mono- or di-lower alkylamino group or a halogen atom, $R^3$ and $R^4$: may be the same or different from each other and each represents a hydrogen atom or a lower alkyl group, n: 0, 1 or 2, m: an integer of 2 to 6, and p: an integer of 1 to 6 or a pharmaceutically acceptable salt thereof.

2. The compound according to claim 1, wherein A is a group represented by a formula $(CH_2)_m$, X is an oxygen atom, n is 2 and $R^1$ is a hydroxyl group.

3. 4-[2,3-Dioxo-7-(1H-imidazol-1-yl)-6-nitro-1,2,3,4-tetrahydroquinoxalin-1-yl]butanesulfate or a pharmaceutically acceptable salt thereof.

4. 3-[2,3-Dioxo-7-(1H-imidazol-1-yl)-6-nitro-1,2,3,4-tetrahydroquinoxalin-1-yl]propanesulfate or a pharmaceutically acceptable salt thereof.

5. A pharmaceutical composition, which comprises any one of the compounds of claims 1 to 4 or a pharmaceutically acceptable salt thereof and a pharmaceutically acceptable carrier.

6. The pharmaceutical composition according to claim 5, wherein the compound is an effective amount of an AMPA receptor antagonist.

7. The pharmaceutical composition according to claim 5, wherein the compound is an effective amount of a kainic acid neurotoxicity inhibitor.

8. The pharmaceutical composition according to claim 5, wherein the compound is an effective amount of an anti-ischemia drug.

9. The pharmaceutical composition according to claim 5, wherein the compound is an effective amount of a psychotropic drug.

* * * * *